(12) United States Patent
Hassan Abdalla

(10) Patent No.: US 9,458,225 B2
(45) Date of Patent: Oct. 4, 2016

(54) METHOD FOR PURIFYING LACTOFERRIN

(71) Applicant: United Arab Emirates University, Al-Ain (AE)

(72) Inventor: Hassan Mohamed Hassan Abdalla, Al-Ain (AE)

(73) Assignee: UNITED ARAB EMIRATES UNIVERSITY, Al-Ain, Abu Dhabi (AE)

( * ) Notice: Subject to any disclaimer, the term of this patent is extended or adjusted under 35 U.S.C. 154(b) by 21 days.

(21) Appl. No.: 13/927,314

(22) Filed: Jun. 26, 2013

(65) Prior Publication Data
US 2015/0005478 A1    Jan. 1, 2015

(51) Int. Cl.
*C07K 14/79*    (2006.01)

(52) U.S. Cl.
CPC ..................................... *C07K 14/79* (2013.01)

(58) Field of Classification Search
None
See application file for complete search history.

(56) References Cited

U.S. PATENT DOCUMENTS

| | | | | |
|---|---|---|---|---|
| 4,436,658 A | * | 3/1984 | Peyrouset | A23J 1/205 426/271 |
| 4,668,771 A | * | 5/1987 | Kawakami | C07K 14/79 435/70.21 |
| 4,791,193 A | | 12/1988 | Okonogi et al. | |
| 5,861,491 A | | 1/1999 | Nuijens | |
| 5,919,913 A | | 7/1999 | Nuyens et al. | |
| 6,096,870 A | * | 8/2000 | Mozaffar | A21D 2/263 426/41 |
| 2002/0165128 A1 | * | 11/2002 | Plaut | A61K 39/102 424/184.1 |

FOREIGN PATENT DOCUMENTS

WO    2006/119644 A1    11/2006

OTHER PUBLICATIONS

Foley et al., Analytical Biochem., 1987, 162, 296-300.*
Querinjean, P., Masson, P. L. & Heremans, J. F., "Molecular Weight, Single-Chain Structure and Amino Acid Composition of Human Lactoferin", (1971) Eur. J. Biochem. 20, 420-425, received Mar. 26, 1971.
Johansson, B. G., "Isolation of Crystalline Lactoferrin from Human Milk", (1969) Acta Chem. Scand. 23, 683-684, received Jan. 20, 1969.
Johansson, B., "Chromatographic Separation of Lactalbumin from Human Milk Whey on Calcium Phosphate Columns", Apr. 5, 1958, Nature, Lond., 181, pp. 996-997.
Torres AR, Peterson EA, Evans WH, Mage MG, and Wilson SM, "Fractionation of granule proteins of granulocytes by copper chelate chromatography", Biochim Biophys Acta 576:385-392, 1979, received Jun. 14, 1978.
Roberts T. K., Boursnell J. C., "The Isolation and Chacterization of Lactoferrin From Soy Milk and Boar Seminal Plasma" J. Reprod. Fertil. 1975, 42, 579-582, received Aug. 13, 1974.
ZaGulski T., Jarzj\Bek .Z., Zagulska A., Jedra .J., "A simple method of obtaining large quantities of bovine lactoferrin", (1979) Prace i Materialy Zootechniczne 20, 87-101, received Sep. 5, 1977.
Moguilevsky, N., Retegui, L.A. & Masson, P. L., "Comparison of human lactoferrins from milk and neutrophilic leucocytes", (1985) Biochem. J. 229,353-359, accepted Mar. 21, 1985.
Ekstrand, B., Bjorck, L., "Fast protein liquid chromatography of antibacterial components in milk", J. Chromatogr. 358, (1986) 429-433, received Feb. 14, 1986.
Foley and G.W. Bates, "The purification of lactoferrin from human whey by batch extraction", Anal. Biochem., 162 (1987), p. 296, received Oct. 9, 1986.
Yoshida and Ye-Xiuyun, "Isolation of Lactoperoxidase and Lactoferrins from Bovine Milk Acid Whey by Carboxymethyl Cation Exchange Chromatography", (10) (1991) J. Dairy Sci. 74: 1439-1444, accepted Dec. 7, 1990.
Kawakami, H., H. Shinmoto, S. Dosako and Y. Sago, 1987, "One-step isolation of lactoferrin using immobilized monoclonal antibodies", J. Dairy Sci., 70: 752-759, accepted Dec. 29, 1986.
Hutchens, T.W, J.F. Henry and T.T. Yip, "Purification and characterization of intact lactoferrin found in the urine of human milk-fed preterm infants" Clin. Chem., 35/9: 1928-1933 (1989), accepted Jun. 29, 1989.
Chen, J.P. and Wang, C.H., "Microfiltration affinity purification of lactoferrin and immunoglobulins from cheese whey", J. Food Sci. 56:701-706 (1991).
Bezwoda, W.R. and N. Mansoor, "Isolation and characterisation of lactoferrin separated from human whey by adsorption chromatography using Cibacron Blue F3G-A linked affinity adsorbent", Clin. Chem. Acta, 157 (1986) 89-93, received with revision on Jan. 18, 1986.
Pahud, J.J. and H. Hilpert, "Affinity chromatography of lactoferrin on immobilized ferritin", Protides Bioi. Fluids Proc. Colloquium, 23: 571-574 (1976).
Blackberg, L. and 0. Hernell, "Isolation of lactoferrin from human whey by a single chromatographic step", Federation Eur. Biochem. Soc. Lett., Jan. 1980, vol. 109, No. 2, pp. 180-183.
M.Drackova, I. Borkovcova, B. Janstova, M. naiserova, H. Pridalova, P. Navrtilova and I. Vorlova, "Determination of Lactoferrin in Goat Milk by HPLC Method", Czech J. Food Sci. vol. 27, 2009, Special Issue.

(Continued)

*Primary Examiner* — James H Alstrum Acevedo
*Assistant Examiner* — Roy Teller
(74) *Attorney, Agent, or Firm* — Katten Muchin Rosenman LLP

(57) ABSTRACT

The present invention relates to a method for purifying lactoferrin, which is a pharmacologically important milk protein having various physiological activities, from a secretory fluid containing lactoferrin.

10 Claims, 4 Drawing Sheets

(56) References Cited

OTHER PUBLICATIONS

C. Nick Felix Vajdos, 'Lanette Fee,' Gerald Grimsley, and Theronica Gray "How to measure and predict the molar absorption coefficient of a protein", Protein Science (1995), 4:2411-2423, accepted Sep. 8, 1995.

Gerald D. Fasman (Editor), CRC Practical Handbook of Biochemistry and Molecular Biology, CRC Press (US: 1989), p. 275.

J. Kong and S. Yu, "Fourier Transform Infrared Spectroscopic Analysis of Protien Secondary Structures", Acta Biochim. Biophys. Sin., 2007, 39, 549-559, accepted Apr. 29, 2007.

W. K. Surewicz, H. H. Mantsch and D. Chapman, "Determination of Protien Secondary Structure by Fourier Transform Infared Spectroscopy: A Critical Assessment", Biochemistry, Jan. 19, 1993, vol. 32, No. 2, 389-393.

H. U. Gremlich and B. Yan (editors), "Infrared and Raman Spectroscopy of Biological Materials", Practical Spectroscopy Series, CRC Press, Taylor and Francis group, 2000, vol. 24, pp. 329-330.

Hiromi Tanaka, Gou Yoshida, Yousuke Baba, Kenta Matsumura, Hiroshi Wasada, Jirou Murata, Mfna Agawa, Shuji Itakura, Akio Enoki, "Characterization of a hydroxyl-radical-producing glycoprotein and its presumptive genes from the white-rot basidiomycete Phanerochaete chrysosporium", J. of biotechnology 128 (2007) 500-501, accepted Dec. 4, 2006.

Med. Dr. Ferdinand Rose "Ueber die Verbindungen des Eiweiss mit Metalloxyden" Annalen der Physik 1833, 104 (5):132-142.

Wu Mian-bin and Xu Yin-Jun, "Isolation and Purification of Lactoferrin and Immunoglobulin G from Bovine Colostrum with Serial Cation-Anion Exchange Chromatography", Biotechnology and Bioprocess Engineering, 2009, vol. 14, pp. 155-160.

International Search Report for International Application No. PCT/IB2014/062596 with a mailing date of Nov. 17, 2014.

Written Opinion of the International Searching Authority for International Application No. PCT/IB2014/062596 with a mailing date of Nov. 17, 2014.

* cited by examiner

METHOD FOR PURIFYING LACTOFERRIN

FIELD OF INVENTION

The present invention relates to a method for purifying lactoferrin, which is a pharmacologically important milk protein having various physiological activities, from a secretory fluid containing lactoferrin.

BACKGROUND OF THE INVENTION

Lactoferrin (LF) is an iron-binding glycoprotein present in secretory (exocrine) fluids such as milk. It has a variety of physiological activities such as bacteriostasis against pathogenic bacteria, adjusting function of leukocyte differentiation, build-up function of germicidal power, multiplicative function of lymphocyte and adjusting function of iron absorption. For that reason, it can be said that lactoferrin is important not only from a nutritional viewpoint but also a pharmacological viewpoint.

As a result, many attempts have previously been made to develop methods for purifying lactoferrin from milk. However, since lactoferrin has a very reactive molecular structure and interacts strongly with other milk proteins, it has been difficult to purify lactoferrin with high purity and in a high yield by a simple and easy operation.

In other words, in order to separate high-purity lactoferrin, an intricate process and a long period of time is necessary. In addition, the recovery efficiency of lactoferrin is disadvantageously low.

The scientific literature reports several of protocols for the isolation of lactoferrin from milk. A number of these involve isolation of LF from a natural source using ion-exchange chromatography followed by salt elution. Querinjean et al.[1], report isolation of human lactoferrin (hLF) from human milk on CM Sephadex C-50 followed by elution with 0.33M NaCl. Johannson employed CM Sephadex C-50 for purification of LF[2] and has also reported the use of calcium phosphate for LF purification[3]. Torres et al[4], report lactoferrin isolation from guinea pig milk. The milk was pre-treated by centrifugation to remove fats and to sediment the casein. A Whatman CM-52 column was used, and lactoferrin was eluted with 0.5M NaCl/5 mM sodium phosphate, pH 7.5. Roberts and Boursnell[5], report lactoferrin isolated from defatted sow's milk. CM-Sephadex was added to an ammonium ferrous sulfate precipitate of the milk, and the bound lactoferrin was eluted with 0.5M NaCl/20 mM phosphate at pH 7 followed by a second CM-Sephadex fractionation from which the lactoferrin was eluted with 0.4M NaCl. Zagulski et al.[6], report bovine lactoferrin isolated from bovine milk. Defatted bovine milk was mixed with CM-Sephadex C-50, and lactoferrin was eluted from the column with 0.5M sodium chloride/0.02M sodium phosphate at pH 7. Moguilevsky et al.[7], report lactoferrin isolated from human milk, using CM-Sephadex chromatography and elution with 1M sodium chloride. Ekstrand and Bjorck[8], report lactoferrin isolated from human colostrum and bovine milk. Defatted bovine or human milk was acidified, adjusted to pH 7.8 and applied to a Mono S™ column. The bovine or human lactoferrin was eluted with a continuous salt gradient of 0M to 1M NaCl. The purification of human lactoferrin from bovine lactoferrin was not reported. Foley and Bates[9], report isolation of lactoferrin from human colostrum whey. The whey was mixed with a weak ion-exchange resin (cellulose phosphate) and proteins were eluted with a stepped salt and pH gradient. Lactoferrin was eluted with 0.25M NaCl/0.2M sodium phosphate at pH 7.5. Further, Yoshida and Ye-Xiuyun[10], disclosed the isolation of lactoferrin by ion exchange on carboxymethyl cation resin using 0.05M phosphate buffer at pH 7.7 with a linear gradient of 0M to 0.55M NaCl. The carboxymethyl-Toyopearl column adsorbed only lactoperoxidase and lactoferrin from the albumin fraction of bovine milk acid whey. Lactoferrin was eluted between 0.4M and 0.55M NaCl and was separated into two components; lactoferrin A and lactoferrin B. Other methods, including affinity chromatography, have also been reported. For example, in Kawakami et al.[11], affinity chromatography of LF with monoclonal antibodies to human or bovine lactoferrin was reported. Human lactoferrin was isolated from human colostrum and bovine lactoferrin from bovine milk or cheese whey. (See also U.S. Pat. No. 4,668,771, the content of which is incorporated herein by reference). Hutchens et al.[12], lactoferrin was isolated from the urine of human milk fed preterm infants with single-stranded DNA on an affinity column. Additionally, Chen and Wang[13], reported a process combining affinity chromatography with membrane filtration to isolate lactoferrin from bovine cheese whey using heparin-Sepharose to bind lactoferrin. Cheese whey was diluted with a binding buffer and added to the heparin-Sepharose material. The slurry was microfiltered, and the lactoferrin was eluted with 5 mM veronal-hydrochloride/0.6M NaCl at pH 7.4. Bezwoda et al.[14], report the use of Cibacron Blue F3GA resin for purification of LF. The purification of ferritin (Pahud et al.[15]) and heparin (Blackberg.[16]) from milk has also been reported.

SUMMARY OF THE INVENTION

There exists a need in the art for simple and efficient methods for purification of lactoferrin from secretory fluids such as milk. It is one object of the invention to provide methods and compositions for economical and efficient purification of lactoferrin from secretory fluids, such as bovine milk, in a high yield and with high purity. The lactoferrin may be for use as a pharmaceutical or food additive. The present invention fulfills these and other needs.

A first object of the present invention is to provide a method for purifying lactoferrin from a secretory fluid on an industrial scale by a simple and easy operation. A second object of the present invention is to provide a method for purifying lactoferrin from a secretory fluid, such as milk, extremely effectively in a high yield and a high purity.

Thus, in a first aspect the present invention provides a method of purifying lactoferrin from a secretory fluid, the method comprising alkalizing the secretory fluid, contacting the alkalized secretory fluid with air, and precipitating lactoferrin from the alkalized secretory fluid using an organic solvent.

Optionally, the precipitated lactoferrin may be separated from the liquid fraction by any suitable technique. Suitable techniques include but are not limited to decantation and filtration.

Preferably, the secretory fluid is milk. More preferably, the secretory fluid is milk selected from bovine, cameline, caprine (goat) or human milk.

Preferably, the secretory fluid is alkalized using an alkali selected from potassium hydroxide or sodium hydroxide. Most preferably, the secretory fluid is alkalized using sodium hydroxide.

Preferably, the method further comprises stirring the alkalized secretory fluid in a carbon dioxide enriched atmosphere.

Preferably, the method further comprises removing the lipid fraction after contacting the alkalized secretory fluid with air.

Preferably, the organic solvent is acetone. More preferably, the volume of organic solvent used is twice the volume of the alkalized secretory fluid.

Preferably, the method comprises the steps of:
(a). mixing the secretory fluid with an alkali;
(b). stirring the mixture obtained in step (a) in the presence of carbon dioxide;
(c). removing the lipid fraction;
(d). adding a volume of an organic solvent to the aqueous fraction to obtain a precipitate;
(e). separating the liquid fraction from the precipitate;
(f). rinsing the precipitate with organic solvent; and
(g). removing residual organic solvent.

Optionally, the resulting precipitate may be lyophilized in deionised water.

In a second aspect, the present invention relates to a lactoferrin containing composition obtained by the method described in the first aspect.

In a third aspect, the present invention provides a method of purifying lactoferrin from a secretory fluid, the method comprising:
(a). mixing the secretory fluid with an alkali;
(b). stirring the mixture obtained in step (a) in the presence of carbon dioxide;
(c). removing the lipid fraction;
(d). adding a volume of an organic solvent to the aqueous fraction to obtain a precipitate;
(e). separating the liquid fraction from the precipitate;
(f). rinsing the precipitate with organic solvent; and
(g). removing residual organic solvent.

Optionally, the resulting precipitate may be lyophilized in deionised water.

Preferably, the secretory fluid is milk or a milk by-product. More preferably, the secretory fluid is milk selected from bovine, cameline, caprine (goat) or human milk.

Preferably, the alkali is selected from potassium hydroxide or sodium hydroxide. Most preferably, the secretory fluid is alkalized using sodium hydroxide.

Preferably, the organic solvent is acetone.

Preferably, the volume of organic solvent added is twice the volume of the aqueous fraction.

In a fourth aspect, the present invention relates to a lactoferrin containing composition obtained by the method described in the third aspect.

DETAILED DESCRIPTION

Figure 1:
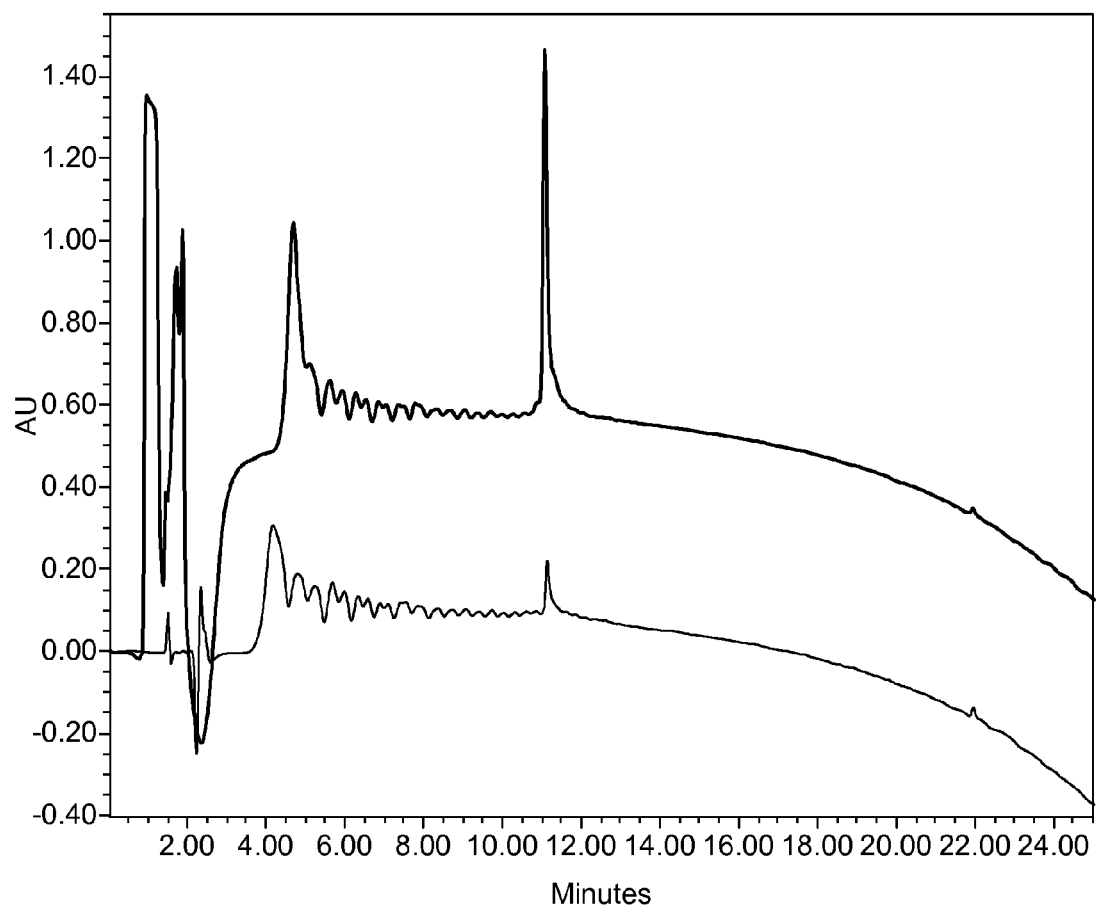
FIG. 1: HPLC elution profile of a lactoferrin sample prepared by the method described herein (top) and lactoferrin standard purchased from Sigma (bottom).

Thus there exists a need in the art for simple and efficient methods for purification of lactoferrin from secretory fluids, in particular milk. Existing methods for lactoferrin purification typically involve the use of ion exchange resins such as CM-Sephadex. These methods are time-consuming and difficult to carry out, particularly at large scales.

It is one object of the invention to provide methods and compositions for economical and efficient purification of lactoferrin from secretory fluids, such as bovine milk, for use as a pharmaceutical or food additive. The present invention fulfills these and other needs.

Thus, in a first aspect the present invention provides a simple and efficient method of purifying lactoferrin from a secretory fluid, the method comprising alkalizing the secretory fluid, contacting the alkalized secretory fluid with air, and precipitating lactoferrin from the alkalized secretory fluid using an organic solvent. Without wishing to be bound by any particular theory, the inventors consider that the present method works via a combination of factors. The alkalization of the secretory fluid serves to break down bonds between the lipids and lactoferrin and to enhance the incorporation of carbonate ions in solution. The increased availability of carbonate ions increases the ability of lactoferrin to chelate iron ions, which in turn allows the protein to be precipitated upon solvent addition.

Advantageously, the secretory fluid does not need to be defatted before use in the presently described method.

Optionally, the precipitated lactoferrin may be separated from the liquid fraction by any suitable technique. Suitable techniques include but are not limited to decantation and filtration.

The described method results in purification of lactoferrin from a lactoferrin-containing secretory fluid, such as milk. Various sources of milk may be used, including but not limited to bovine, cameline, caprine (goat) or human milk.

In certain embodiments, the lipid fraction may be removed after contacting the alkalized secretory fluid with air.

In another embodiment, the method further comprises stirring the alkalized secretory fluid in a carbon dioxide enriched atmosphere.

A particularly preferred embodiment of the described method comprises the steps of:
(a). mixing the secretory fluid with an alkali;
(b). stirring the mixture obtained in step (a) in the presence of carbon dioxide;
(c). removing the lipid fraction;
(d). adding a volume of an organic solvent to the aqueous fraction to obtain a precipitate;
(e). separating the liquid fraction from the precipitate;
(f). rinsing the precipitate with organic solvent; and
(g). removing residual organic solvent.

Optionally, the precipitate may be lyophilized in deionised water.

In a second aspect, the present invention relates to a lactoferrin containing composition obtained by the method described in the first aspect.

In a third aspect, the present invention provides a method of purifying lactoferrin from a secretory fluid, the method comprising:
(a). mixing the secretory fluid with an alkali;
(b). stirring the mixture obtained in step (a) in the presence of carbon dioxide;
(c). removing the lipid fraction;
(d). adding a volume of an organic solvent to the aqueous fraction to obtain a precipitate;
(e). separating the liquid fraction from the precipitate;
(f). rinsing the precipitate with organic solvent; and
(g). removing residual organic solvent.

Optionally, the precipitate may be lyophilized in deionised water.

Preferably, the secretory fluid is milk or a milk by-product. More preferably, the secretory fluid is milk selected from bovine, cameline, caprine (goat) or human milk.

Preferably, the alkali is selected from potassium hydroxide or sodium hydroxide.

Preferably, the organic solvent is acetone.

Preferably, the volume of organic solvent added is twice the volume of the aqueous fraction.

In a fourth aspect, the present invention relates to a lactoferrin containing composition obtained by the method described in the third aspect.

The terms "secretory fluid" and "exocrine fluid" are used herein interchangeably. As used herein, they are intended to mean any fluid secretion from an animal. Such secretions include but are not limited to milk, colostrum, urine, saliva, sweat, tears, sebum, bile (gall), and pancreatic juice. The presently described method may also be used with by-products of secretory fluids. In particular, the present invention may be used with milk by-products, including but not limited to milk whey.

The term "alkalizing" as used herein is intended to mean the process of increasing the pH of a solution. This may be achieved by any suitable means, for example by the addition of an alkali or a base to the solution.

The term "organic solvent" is intended to encompass any non-aqueous solvent, both polar and non-polar. Examples of non-polar solvents include pentane, cyclopentane, hexane, cyclohexane, benzene, toluene, 1,4-dioxane, chloroform and diethyl ether. Examples of polar solvents include dichloromethane (DCM), tetrahydrofuran (THF), ethyl acetate, acetone, dimethylformamide (DMF), acetonitrile (MeCN), dimethyl sulfoxide (DMSO), propylene carbonate, formic acid, n-butanol, isopropanol, n-propanol, ethanol, methanol, acetic acid and nitromethane. A particularly preferred solvent is acetone because it has a medium-high dipole moment ($\mu$=2.88), large dielectric constant ($\in$=20.7) and low boiling point (56.5° C.).

EXAMPLES

The present invention will now be described in detail by way of the following non-limiting examples.

Purification of Lactoferrin 15 ml of 40% sodium hydroxide solution was mixed into 250 mL bovine milk to give a NaOH concentration of 24 g/L, and the whole was stirred for 1 hour at room temperature and open to air. The solution was then left overnight to capture carbon dioxide from air at room temperature. After that the solution turned red due to metal chelating and the fat separated on the top. Fat was separated by decantation then filtration using Whatman filter paper grade 1. To the filtrate was added twice its volume of acetone: the lactoferrin precipitated at the bottom. The liquid layer was decanted leaving precipitated lactoferrin. The precipitate was rinsed several times with acetone to remove residual water. The remaining acetone was removed by evaporation under vacuum at low temperature (−40° C.). The precipitate was then lyophilized in deionized water.

Lactoferrin obtained by this method was glycoprotein contain about 20% lactoferrin, 25% carbonate, 5% metals and 50% glycan. The total yield of lactoferrin obtained by this method was about 15 grams. Similar results were achieved when the method was repeated with milk from other sources and with milk by products.

Characteristic of Isolated Lactoferrin:
Protein Content:

The protein concentration of the Lactoferrin preparation was determined by the Protein-Biuret Method[24] using bovine serum albumin (BSA) as standard. The results of three samples are shown in table 1:

TABLE 1

| \multicolumn{5}{c}{Results of Biuret test} |
|---|---|---|---|---|
| Weight of Standard. | Absorbance. of Standard | Weight of sample | Absorbance. of Sample | % protein |
| 0.5011 | 0.4437 | 0.4910 | 0.1039 | 22.61% |
| 0.5134 | 0.4747 | 0.5023 | 0.0902 | 19.19% |
| 0.4981 | 0.4597 | 0.5001 | 0.0981 | 20.96% |
| Average | | | | 20.92% |

Chromatographic Purity:

For HPLC determination of the lactoferrin separation module Alliance 2695 with diode-array detector PDA 2996 (Waters, Millford, USA) was used. Detection was carried out at the wavelength 205 nm. Separation was performed on a chromatographic column Symmetry-C18, 4.6×250 mm, 5 μm particle size (Waters, USA). Linear gradient and flow rate 1 ml/min were used. Mobile phase A consisted of water/acetonitrile/trifluoroacetic acid (95:5:0.1) and mobile phase B water/acetonitrile/trifluoroacetic acid (5:95:0.1). The column temperature was set at 45° C. and injection volume was 20 μl. Data were collected and evaluated by software Empower (Waters, Millford, USA). An external standard method for quantification analytes was used (lactoferrin, sigma, L9507, >85% SDS-PAGE)[17]. The resulting elution is shown in FIG. 1.

Results:

Average values of lactoferrin in the obtained precipitate was 20.8%. These value was approximately the same obtained in protein content.

UV-Visible Spectroscopy

Figure 2:
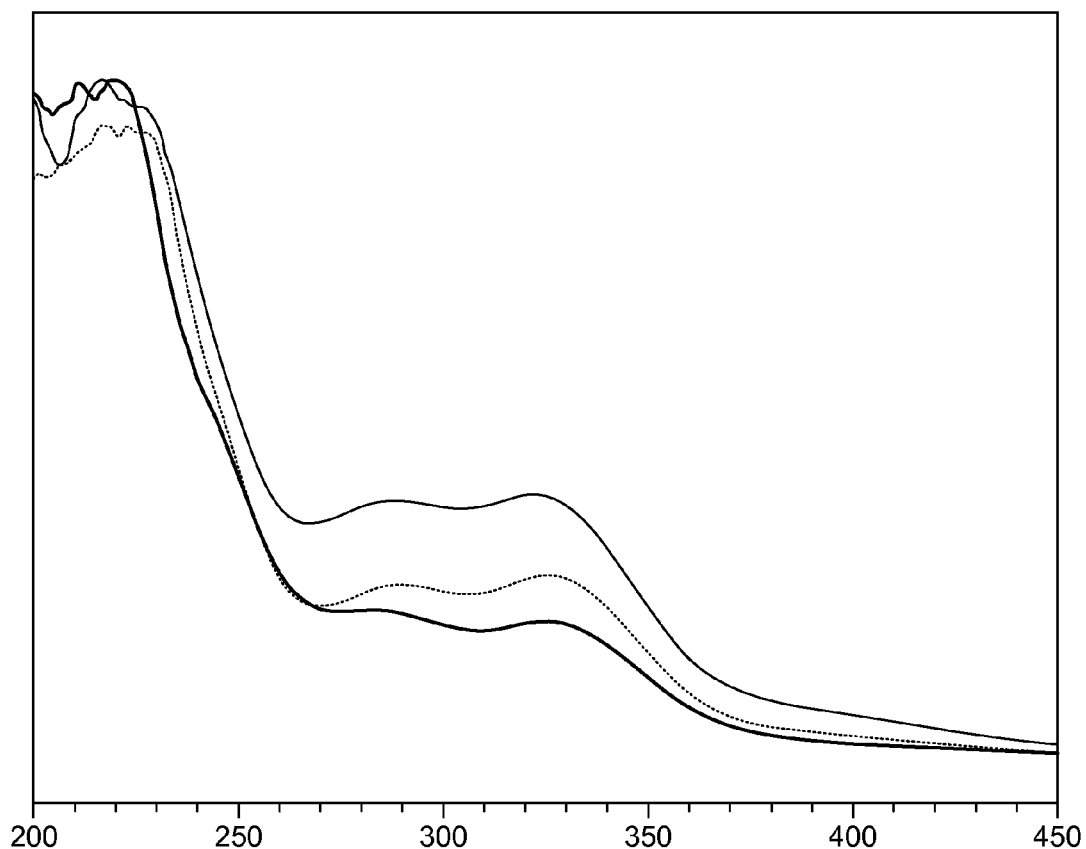
FIG. 2: UV-visible absorption spectrum of a lactoferrin sample prepared by the method described herein.

The spectra characterization of lactoferrin was carried out by scanning the precipitate (2 mg/ml in deionized water) in the range of 200-600 nm using Varian spectroscopy. As shown in FIG. 2, Lactoferrin shows two characteristic maximum band at 280 and 330 nm.

Commonly, the optical absorbance of protein is measured at 280 nm. At this wavelength, the absorbance of protein is mainly due to the amino acids tryptophan, tyrosine and cysteine with their molar absorption coefficients decreasing in that order. Of course, the molar absorption coefficient of the protein itself at 280 nm will depend upon the relative concentrations of these three amino acids. Therefore, different proteins can have different absorption coefficients and even the wavelength of the maximum absorbance may differ. This fact can be used to help identify different types of proteins by relatively fast and simple optical tests.

According to Pace et al.[18] the absorbance of a protein at 280 nm depends on the content of Trp, Tyr, and cystine (disulfide bonds). The extinction coefficient at 280 nm of a folded protein in water ($\in$ at 280 nm) can best be predicted with this equation:

$$\in(280)\ (M^{-1}\ cm^{-1}) = (\#Trp)(5,500) + (\#Tyr)(1,490) + (\#cystine)(125).$$

Extinction Coefficient for lactoferrin: $\in^{\mu M}$=0.11096 (280 nm).[19]

The concentration of a protein solution is most often done by measuring the absorbance, A, near 280 nm and using the Beer-Lambert law:

$$A = \in l C$$

where

∈ is s the molar extinction coefficient ($M^{-1} cm^{-1}$), l is the pathlength (cm), and C is the protein concentration (M). This is an excellent method for measuring protein concentrations provided that an accurate value of ∈ is available.

The absorption for 2 mg/ml precipitate was 1.2

Substitution this value in equation (1) gives the molarity of the protein 1.7=0.11096*C

C=153.2*$10^{-5}$ M

MW=C/con. (mg/ml)

MW=153.2/2=76.6 KD

This value is in good agreement with the value obtained from amino acid analysis (see below).

Amino Acid Analysis:

The amino acid composition of the precipitate was determined by hydrolyzing 50 mg samples of precipitate in 6 M HCl under reduced pressure for 24 hours at 110° C. (18) and performing the analysis on UPLC[19].

The results of the amino acids are summarized in table 2:

TABLE 2

|   | pmole/µl | M.W. of amino acid | mg acid/ ml ppt | Mole residue | Res/mole | Res wt (—H2O) |   |
| --- | --- | --- | --- | --- | --- | --- | --- |
| His | 1.09213 | 155.20 | 0.169499 | 1.6894 | 12 | 137.2 | 1646.4 |
| Ser | 6.87349 | 105.09 | 0.722335 | 7.1995 | 51 | 87.1 | 4442.1 |
| Arg | 3.07177 | 174.20 | 0.535102 | 5.3333 | 37 | 156.2 | 5779.4 |
| Gly | 10.33357 | 75.07 | 0.775741 | 7.7318 | 54 | 57.1 | 3083.4 |
| Asp | 9.05944 | 132.12 | 1.196933 | 11.9299 | 84 | 114.1 | 9584.4 |
| Glu | 7.8832 | 146.14 | 1.152051 | 11.4825 | 81 | 128.1 | 10376.1 |
| Thr | 1.5925 | 119.12 | 0.189699 | 1.8907 | 13 | 101.1 | 1314.3 |
| Ala | 10.82458 | 89.09 | 0.964362 | 9.6118 | 68 | 71.1 | 4834.8 |
| Pro | 3.91014 | 115.13 | 0.450174 | 4.4869 | 32 | 97.1 | 3107.2 |
| Cys | 3.96604 | 121.20 | 0.480684 | 4.7910 | 34 | 103.2 | 3508.8 |
| Lys | 4.9413 | 146.20 | 0.722418 | 7.2003 | 51 | 128.2 | 6538.2 |
| Tyr | 1.58444 | 181.20 | 0.287101 | 2.8615 | 20 | 163.2 | 3264 |
| Met | 0.43121 | 149.21 | 0.064341 | 0.6412 | 5 | 131.2 | 656 |
| Val | 5.48028 | 117.15 | 0.642015 | 6.3989 | 45 | 99.1 | 4459.5 |
| Ileu | 2.03359 | 131.17 | 0.266746 | 2.6586 | 19 | 113.2 | 2150.8 |
| Leu | 7.82288 | 131.17 | 1.026127 | 10.2274 | 72 | 113.2 | 8150.4 |
| Phe | 2.34715 | 165.19 | 0.387726 | 3.8644 | 27 | 147.2 | 3974.4 |
|   |   |   | 10.03305 |   |   |   | 76870.2 |

As shown in the table, the amino acid mole percent is resemble that in literature, this data can be used also to estimate the protein concentration of the unknown protein sample (20.661%) which confirm the previous data obtained.

The molecular weight of the protein estimated is about 76870 Daltons (76.87 kDa).

Fourier-Transform Infrared Spectroscopy (FTIR)

Figure 3:
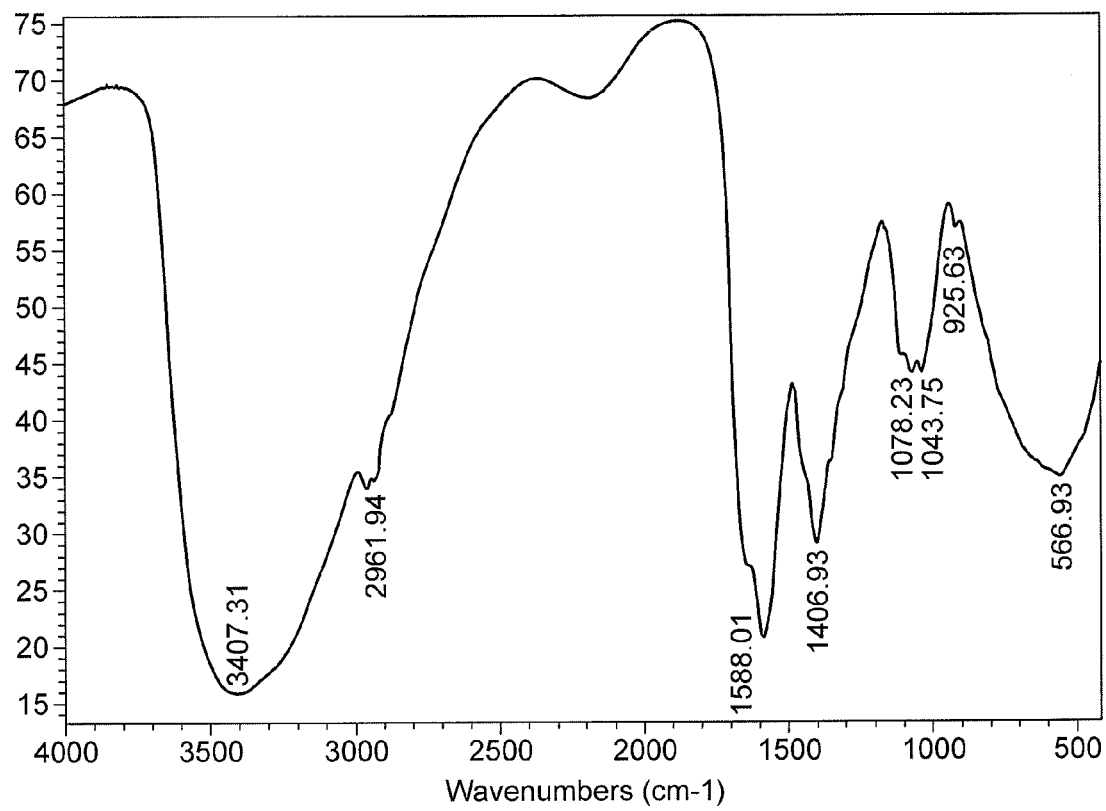
FIG. 3: Fourier transform infrared spectroscopy spectrum of a lactoferrin sample prepared by the method described herein.

FIG. 3 shows the FTIR spectra of the resultant precipitate. The characteristic stretching and bending vibrations arising due to amide bonds which link amino acids are assigned as amide I (1600-1690 $cm^{-1}$), amide II (1480-1575 $cm^{-1}$), amide III (1229-1301 $cm^{-1}$) and amide A (~3300 $cm^{-1}$)[20]. The band appearing at ~700 cm can be assigned to —$NH_2$ and —NH wagging and that at ~2960 $cm^{-1}$ is due to C—H vibrations[21]. (C=O stretching of $COO^-$. Other bands are those at ~1400 $cm^{-1}$), ~1468 $cm^1$ (C—H deformation of >CH 2), and ~3500 $cm^{-1}$ (O—H stretching)[27]. As Lf is a glycoprotein, the broad structure from 900-1200 $cm^{-1}$ is due to C—O, C—C stretches and C—O—H, C—O—C deformation of carbohydrates[22]. In general, the cluster spectrum is broader than the protein and several features are merged.

Carbonate Content

Figure 4:
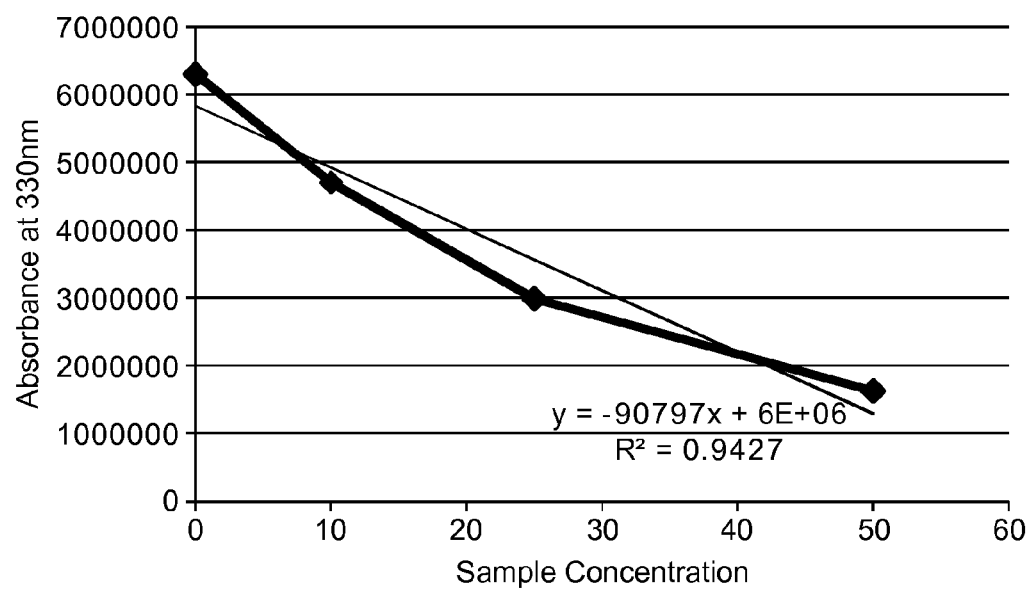
FIG. 4: This figure demonstrates the change in absorbance at 330 nm (vertical axis) versus the concentration of sample.

The carbonyl groups, other than those in the peptide bonds, were assayed by the method described in Uchida[23] et al., with some modifications. Distilled water (500 µl) containing 0, 1, 2.5, or 5 mg of sample was added to 0.1% (w/v) 2,4-dinitrophenylhydrazine in 2N HCl. After 1 h at room temperature, 500 µl of 20% (w/v) trichloroacetic acid (TCA) were added to each assay mixture. Following centrifugation at 9500×g for 10 min, the supernatants were detected by HPLC. A standard curve was prepared using 2,4-dinitrophenylhydrazine (500 µl), distilled water (500 µl), and 20% (w/v) TCA (500 µl). The number of carbonyl groups was calculated based on the rate of the decrease in absorbance after injection in HPLC at 330 nm (as shown in FIG. 4).

TABLE 3

| Component | Regression equation a C (mg/mL) | $R^2$ | Value at zero Y (µg/mL) | Carbonate equivalent | % (Carbonate) | Mole/ mole LF |
| --- | --- | --- | --- | --- | --- | --- |
| $HCO_3^-$ | Y = −90797x + 6E+06 | 0.942 | 66.08 | 660.8 µg sample contain 153 µg HCO3 | 23.15% | 12 |

Metal Analysis:

Metal content of lactoferrin is determined by ICP after digestion in a microwave oven.

The results are shown in table 4:

TABLE 4

| Metal content of precipitate obtained by the described method μg/g | | | | | | | | |
|---|---|---|---|---|---|---|---|---|
| Al | Ca | Cu | Fe | K | Mg | Na | P | Zn |
| 2.55 | 91.40 | 4.09 | 10.20 | 10516.8 | 8.48 | 17701 | 2295.7 | 19.04 |

The present invention is not to be limited in scope by the specific aspects and embodiments described herein. Indeed, various modifications of the invention in addition to those described herein will become apparent to those skilled in the art from the foregoing description and accompanying figures. Such modifications are intended to fall within the scope of the appended claims.

Moreover, all aspects and embodiments described herein are considered to be broadly applicable and combinable with any and all other consistent aspects and embodiments, as appropriate.

Various publications are cited herein, the disclosures of which are incorporated by reference in their entireties.

REFERENCES

1—Querinjean, P., Masson, P. L. & Heremans, J. F. (1971) Eur. J. Biochem. 20, 420-425
2—Johansson, B. G. (1969) Acta Chem. Scand. 23, 683-684
3—Johansson, B. (1958). Nature, Lond., 181, 996.
4—Torres A R, Peters E A, Evans W H, Mage M G, Wilson S M: Fractionation of granule proteins of granulocytes by copper chelate, chromatography. Biochim Biophys Acta 576:385-392, 1979.
5—Roberts T. K., Boursnell J. C.: J. Reprod. Fertil. 1975, 42, 579.
6—ZaGULSKI T., JARZĄBEK Z., ZAGULSKA A., JĘDRA J., 1979—A simple method of obtaining large quantities of bovine lactoferrin. Prace I Materialy Zootechniczne 20, 87-101.
7—Moguilevsky, N., Retegui, L. A. & Masson, P. L. (1985) Biochem. J. 229, 353-359.
8—Ekstrand, B., Bjorck, L., 1986. Fast protein liquid chromatography of antibacterial components in milk. J. Chromatogr. 358, 429-433.
9—Foley and G. W. Bates, The purification of lactoferrin from human whey by batch extraction. Anal. Biochem., 162 (1987), p. 296.
10—Yoshida and Ye-Xiuyun (10) (1991) J. Dairy Sci. 74: 1439.
11—Kawakami, H., H. Shinmoto, S. Dosako and Y. Sago, 1987. One-step isolation of lactoferrin using immobilized monoclonal antibodies. J. Dairy Sci., 70: 752-759.
12—Hutchens, T. W, J. F. Henry and T. T. Yip, 1989. Purification and characterization of intact lactoferrin found in the urine of human milk-fed preterm infants. Clin. Chem., 35: 1928-1933.
13—Chen, J. P. and Wang, C. H. 1991. Microfiltration affinity purification of lactoferrin and immunoglobulins from cheese whey. J. Food Sci. 56:701-706.
14—Bezwoda, W. R. and N. Mansoor, 1986. Isolation and characterisation of lactoferrin separated from human whey by adsorption chromatography using Cibacron Blue F3G-A linked affinity adsorbent. Clin. Chem. Acta, 157: 89-93.
15—Pahud, J. J. and H. Hilpert, 1976. Affinity chromatography of lactoferrin on immobilized ferritin. Protides Biol. Fluids Proc. Colloquium, 23: 571-574.
16—Blackberg, L. and O. Hernell, 1980. Isolation of lactoferrin from human whey by a single chromatographic step. Federation Eur. Biochem. Soc. Lett., 109: 180-183.
17—M. Dračkova, I. Borkovcova, B. Janštova, M. naiserova, H. Přidalova, P. navrtilova and I. Vorlova, "Determination of Lactoferrin in Goat Milk by HPLC Method" Czech J. Food Sci. Vol. 27, 2009, Special Issue.
18—C. NICK FELIX VAJDOS,' LANETTE FEE,' GERALD GRIMSLEY, THERONICA GRAY "How to measure and predict the molar absorption coefficient of a protein" Protein Science (1995), 4:2411-2423.
19—CRC Practical Handbook of Biochemistry and Molecular Biology, CRC Press (US: 1989), p. 275.
20—J. Kong and S. Yu, Acta Biochim. Biophys. Sin., 2007, 39, 549-559.
21—W. K. Surewicz, H. H. Mantsch and D. Chapman, Biochemistry, 1993, 32, 389-393.
22—Infrared and Raman Spectroscopy of Biological Materials. Practical Spectroscopy Series, ed. H. U. Gremlich and B. Yan, CRC Press, Taylor and Francis group, 2000, vol. 24, pp. 329-330.
23—Hiromi Tanaka, Gou Yoshida, Yousuke Baba, Kenta Matsumura, Hiroshi Wasada, Jirou Murata, Mana Agawa, Shuji Itakura, Akio Enoki "characterization of a hydroxyl-radical-producing glycoprotein and its presumptive genes from the white-rot basidiomycete Phanerochaete chrysosporium" J. of biotechnology 128(2007) 500-501.
24—Med. Dr. Ferdinand Rose "Ueber die Verbindungen des Eiweiss mit Metalloxyden" Annalen der Physik 1833, 104(5):132-142

The invention claimed is:

1. A non-chromatographic method of purifying lactoferrin from a secretory fluid, the method comprising alkalizing the secretory fluid and contacting the alkalized secretory fluid with air so as to permit the secretory fluid to capture carbon dioxide from the air, wherein the alkalization of the secretory fluid breaks down bonds between lipids present in the secretory fluid and lactoferrin and enhances the incorporation of carbonate ions in the alkalized secretory fluid, the method further comprising precipitating the lactoferrin from the alkalized secretory fluid using an organic solvent.

2. The method of claim 1, wherein the secretory fluid is milk or a milk by-product.

3. The method of claim 2, wherein the secretory fluid is milk selected from bovine, cameline, caprine (goat) or human milk.

4. The method of claim 1, wherein the secretory fluid is alkalized using an alkali selected from potassium hydroxide or sodium hydroxide.

5. The method of claim 1, wherein the organic solvent is acetone.

6. The method of claim 1, wherein the volume of organic solvent used is twice the volume of the alkalized secretory fluid.

7. The method of claim 1, comprising:
(a) mixing the secretory fluid with an alkali;
(b) stirring the mixture obtained in step (a) in the presence of air;
(e) removing the lipid fraction;
(d) adding a volume of an organic solvent to the aqueous fraction to obtain a precipitate;

(e) separating the liquid fraction from the precipitate;
(f) rinsing the precipitate with organic solvent; and
(g) removing residual organic solvent.

8. The method of claim 7, wherein the resulting precipitate is lyophilized in deionised water.

9. A lactoferrin containing composition obtained by the method of claim 1.

10. The method of claim 1, wherein the increased availability of the carbonate ions in the alkalized secretory fluid increases the ability of lactoferrin to chilate metal ions present in the alkalized secretory fluid, thereby allowing said precipitation of the lactoferrin upon addition of said organic solvent.

* * * * *